United States Patent

Blume et al.

Patent Number: 4,859,230
Date of Patent: Aug. 22, 1989

[54] HALOGENCYCLOPROPYL COMPOUNDS, AND USE AS HERBICIDAL AGENTS

[75] Inventors: Friedhelm Blume; Wilfried Franke; Friedrich Arndt; Richard Rees, all of Berlin, Fed. Rep. of Germany

[73] Assignee: Schering Aktiengesellschaft, Fed. Rep. of Germany

[21] Appl. No.: 108,380

[22] Filed: Oct. 14, 1987

[30] Foreign Application Priority Data

Oct. 14, 1986 [DE] Fed. Rep. of Germany ....... 3635309

[51] Int. Cl.⁴ .................. A01N 43/707; A01N 43/56; A01N 43/54; A01N 43/653
[52] U.S. Cl. ........................................ 71/93; 71/92; 71/95; 71/96; 544/182; 548/371; 548/372; 548/265; 548/144; 548/145; 548/258; 548/264; 548/302; 548/485; 548/369; 548/324; 548/513; 540/579
[58] Field of Search .................. 71/92, 93, 96, 95; 544/182; 548/371, 372, 265, 144, 145, 258, 264, 302, 485, 369, 324, 513; 540/579

[56] References Cited

PUBLICATIONS

Showa Denko K.K., Chemical Abstracts, vol. 99, entry 122461r (1983).
Haga et al., Chemical Abstracts, vol. 103, entry 141975d (1985).
Nagano et al., Chemical Abstracts, vol. 105, entry 42822m (1986).

Primary Examiner—John M. Ford

[57] ABSTRACT

There are described new halocyclopropyl compounds of the general formula I

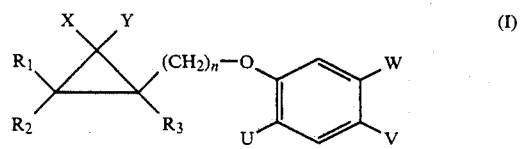

in which $R_1$, $R_2$ and $R_3$, independently of each other, are hydrogen or $C_{1-4}$-alkyl,
X is hydrogen or halogen,
Y is halogen,
n is 0, 1, 2 or 3,
U and V are hydrogen or halogen, and
W is a heterocyclic group of formula

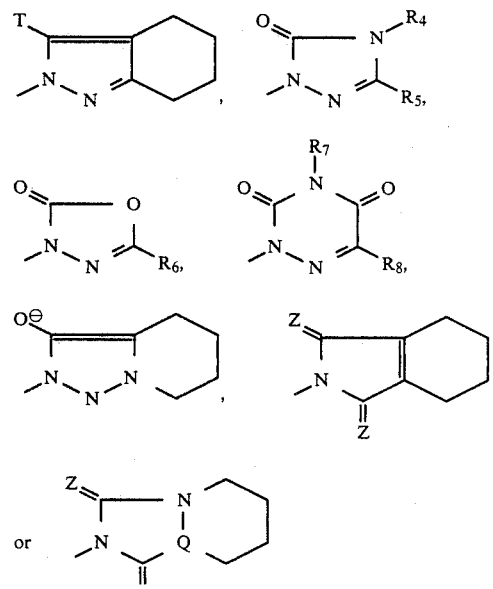

in which
T is halogen, $C_{1-4}$-alkyl, $C_{1-4}$-haloalkyl, CN or $OR_9$
Q is CH or N,
Z is O or S,
$R_4$, $R_5$, $R_6$, $R_7$ and $R_8$ are each a straight, branched or cyclic $C_{1-7}$-alkyl group optionally substituted by up to six halogen atoms, or
$R_4$ and $R_5$, can also together form a 4 to 7 membered ring that is saturated or unsaturated and can contain further hetero atoms, such as O, S or N, and can optionally be substituted by one to three methyl groups or one to six halogen atoms, and
$R_9$ is hydrogen, $C_{1-4}$-alkyl or $C_{1-4}$-haloalkyl, processes for their preparation and their use as herbicide with high selectivity.

20 Claims, No Drawings

HALOGENCYCLOPROPYL COMPOUNDS, AND USE AS HERBICIDAL AGENTS

DESCRIPTION

This invention relates to new halocyclopropyl compounds, their preparation by known methods and their use as herbicides.

It is already known that certain tetrahydroindazoles and tetrahydrophthalimides have herbicidal properties (EP61 741 and 105 721). The activity of these substances in pre- and post-emergent use is good but they suffer from the disadvantage that their compatibility with several crops—such as for example cotton, soybeans and cereals is not sufficient.

It has now been found that halocyclopropyl compounds of the general formula I

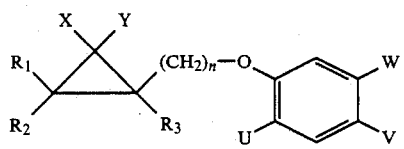

in which
  $R_1$, $R_2$ and $R_3$, independently of each other, are hydrogen or $C_{1-4}$-alkyl,
  X is hydrogen or halogen,
  Y is halogen.
  n is 0, 1, 2 or 3.
  U and V are hydrogen or halogen, and
  W is a heterocyclic group of formula

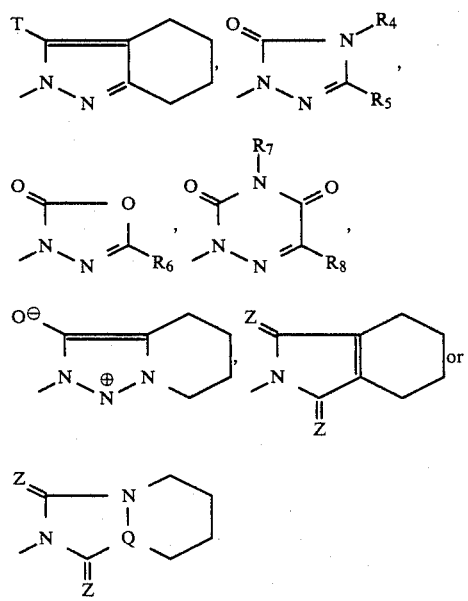

in which
  T is halogen, $C_{1-4}$-alkyl, $C_{1-4}$-haloalkyl, CN or $OR_9$
  Q is CH or N.
  Z is O or S.
  $R_4$, $R_5$, $R_6$, $R_7$ and $R_8$ are each a straight, branched or cyclic $C_{1-7}$-alkyl group optionally substituted by up to six halogen atoms, or
  $R_4$ and $R_5$, can also together form a 4 to 7 membered ring that is saturated or unsaturated and can contain further hetero atoms, such as O, S or N, and can optionally be substituted by one to three methyl groups or one to six halogen atoms, and
  $R_9$ is hydrogen, $C_{1-4}$-alkyl or $C_{1-4}$-haloalkyl,
surprisingly posses outstanding compatibility with rice wheat, soybeans, maize, cotton and barley whilst at the same time showing improved herbicidal activity.

The term "halogen" stands for F, Cl, Br or I. The expression haloalkyl means that one or more hydrogen atoms of the alkyl group are replaced by halogen.

Examples of heterocyclic rings include: pyrrole, oxazole, thiazole, imidazole, pyridine, oxazine, thiazine, pyrimidine, pyrazine, triazine, oxadiazine and thiadiazine as well as their di-, tetra- or preferably hexahydroderivatives.

The compounds of the invention can be prepared in known manner according to the following routes:

(a) A halide of the general formula II

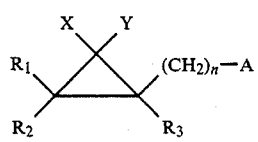

in which $R_1$, $R_2$, $R_3$, X, Y and n have the meanings given in formula I, and A is chlorine, bromine or iodine, is reacted with a phenol of formula III

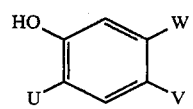

in which U, V and W have the meanings given in formula I.

(b) For the preparation of a compound of formula I, in which W is a 4,5,6,7-tetrahydroindazol-2-yl group, a compound of formula IV

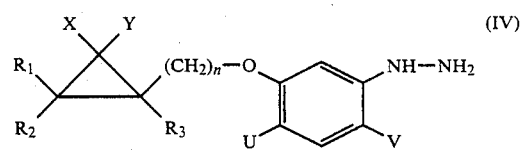

in which $R_1$, $R_2$, $R_3$, X, Y, n, U and V have the meanings given in formula I, is reacted with a compound formula V

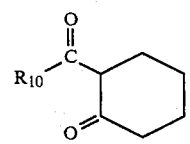

in which $R_{10}$ is $C_{1-4}$-alkyl, $C_{1-4}$-haloalkyl or $C_{1-4}$-alkoxy.

The compounds of formula I, so obtained, in which T is hydroxy can be optionally further modified. For example, by reaction with dialkyl sulphate, compounds in which T is alkoxy can be obtained, and by reaction with a phosphoryl halide, compounds in which T is halogen can be obtained, which by treatment with NaCN can be optionally converted to the corresponding compound in which T is CN.

(c) For the preparation of compounds of formula I, in which W is a 2H-1,2,4-triazolin-3-on-2-yl group, a compound of formula IV

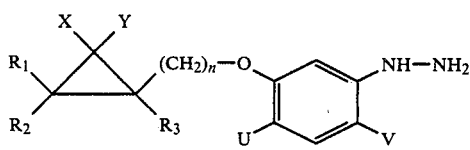 (IV)

in which $R_1$, $R_2$, $R_3$, X, Y, n, U and V have the meanings given in formula I, is reacted with a compound of formula VI

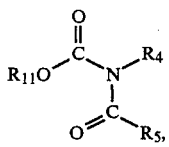 (VI)

in which $R_4$ and $R_5$ have the meanings given in formula I and $R_{11}$ is $C_{1-4}$-alkyl, or a compound of formula IV

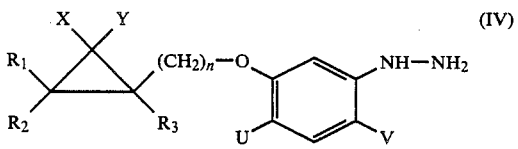 (IV)

in which $R_1$, $R_2$, $R_3$, X, Y, n, U and V have the meanings given in formula I, is reacted with a keto acid of formula XII

 (XII)

in which $R_8$ has the meaning given in formula I, to give a compound of formula XI

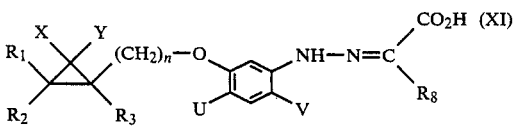 (XI)

in which $R_1$, $R_2$, $R_3$, X, Y, n, U, V and $R_8$ have the meanings given in formula I, which is cyclised by treatment with a phosphoric acid ester azide to give a compound of formula XXIII

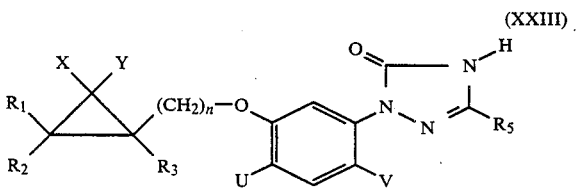 (XXIII)

in which $R_1$, $R_2$, $R_3$, X, Y, n, U, V and $R_5$ have the meanings given in formula I, which is optionally reacted with a compound of formula X

$R_4$-A (X)

in which $R_4$ has the meaning given in formula I and A is chlorine, bromine or iodine.

(d) For the preparation of the compound of formula I, in which W is a 3H-1,3,4-oxdiazol-2-on-3-yl group, a compound of formula IV

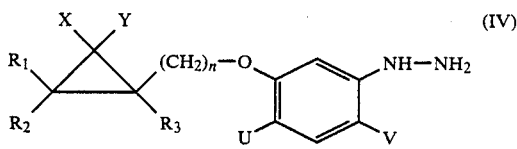 (IV)

in which $R_1$, $R_2$, $R_3$, X, Y, n, U and V have the meanings given in formula I, is reacted with an acid derivative of formula VIII

 (VIII)

in which $R_6$ has the meaning given in formula I and $R_{12}$ is halogen or $C_{1-4}$-alkoxy, to give, as an intermediate, a compound of formula VII

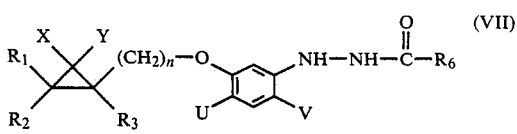 (VII)

in which $R_1$, $R_2$, $R_3$, X, Y, n, U, V and $R_6$ have the meanings given in formula I, which is then reacted with phosgene or its reactive functional derivative.

(e) For the preparation of compounds of formula I, in which W is a 2H,4H-1,2,4-triazine-3,5-dion-2-yl group, a compound of formula IV

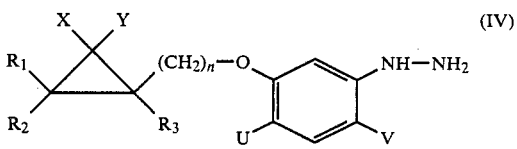 (IV)

in which $R_1$, $R_2$, $R_3$, X, Y, n, U and V have the meanings given in formula I, is reacted with a keto acid of formula XII

 (XII)

in which $R_8$ has the meaning given in formula I, to give a compound of formula XI

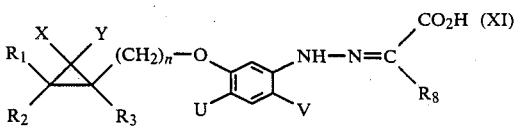 (XI)

in which $R_1$, $R_2$, $R_3$, X, Y, n, U, V and $R_8$ have the meanings given in formula I, which is cyclised by treatment with thionyl chloride or phosphoryl chloride and then with a carbamate ester to give a compound of formula IX

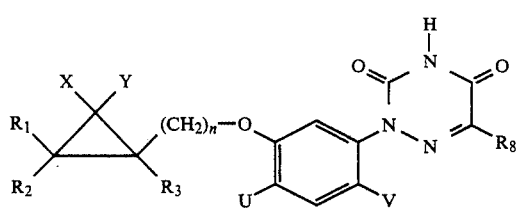

in which $R_1$, $R_2$, $R_3$, X, Y, n, U, V and $R_8$ have the meanings given in formula I, which is reacted with a compound of formula X $$R_7\text{-}A \qquad (X)$$

in which $R_7$ has the meaning given in formula I and A is chlorine, bromine or iodine.

(f) For the preparation of compounds of formula I, in which W is a 4,5,6,7-tetrahydro-2H-1,2,3-triazolo[3,4-a]pyridin-8-ium-3-olat-2-yl group, a compound of formula XV

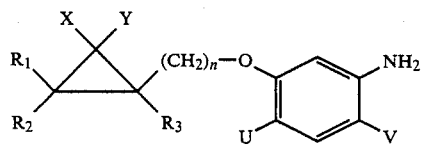

in which $R_1$, $R_2$, $R_3$, X, Y, n, U and V have the meanings given in formula I, is diazotised with nitrous acid, reacted with piperidine-2-carboxylic acid and cyclised with acetic anhydride.

(g) For the preparation of a compound of formula I, in which W is a 1,3,4,5,6,7-hexahydro-2H-isoindole-1,3-dion-2-yl group, a compound of formula XV

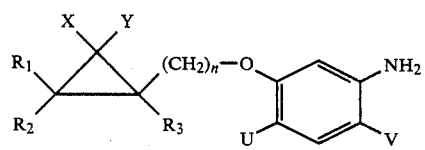

in which $R_1$, $R_2$, $R_3$, X, Y, n, U and V have the meanings given in formula I, is reacted with a compound formula XVI

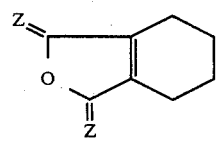

in which Z=O or S.

(h) For the preparation of compounds of formula I, in which W is a 2,3,5,6,7,8-hexahydro-1H-imidazo[1,5-a]-pyridine-1,3-dion-2-yl or a 2,3,5,6,7,8-hexahydro-1H-1,3,4-triazolo[1,2-a]pyridazine-1,3-dion-2-yl group, a compound of formula XV

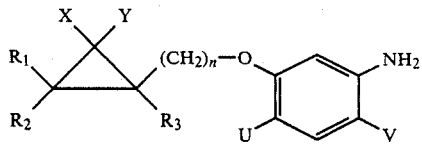

in which $R_1$, $R_2$, $R_3$, X, Y, n, U and V have the meanings given in formula I, is reacted with a compound of formula XVII or XVIII

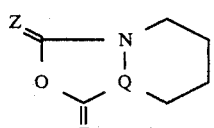

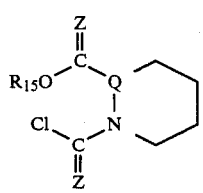

in which Z=O or S, Q is CH or N and $R_{15}$ is $C_{1-4}$-alkyl, or a compound of formula XIX

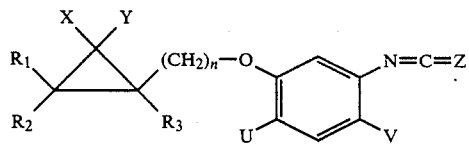

in which $R_1$, $R_2$, $R_3$, X, Y, n, U, V and Z have the meanings given in formula I, is reacted with a compound of formula XX

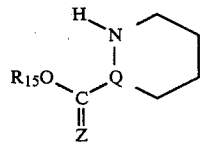

in which Q is CH or N, Z=O or S and $R_{15}$ is $C_{1-4}$-alkyl.

The compound of formula XIX can be prepared by reacting a compound of formula XV

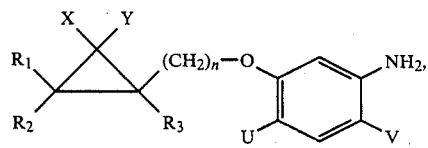

in which $R_1$, $R_2$, $R_3$, X, Y, n, U and V have the meanings given in formula I, with phosgene or thiophosgene.

(i) A compound of formula XXI

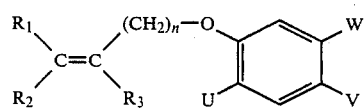

in which $R_1$, $R_2$, $R_3$, U, V, W and n have the meanings given in formula I, is reacted with a halogenated methane derivative of formula XXII

 (XXII)

in which X and Y have the meanings given in formula I, and B is hydrogen or

in which M is an alkali metal.

The reaction according to process variant (a) is suitably carried out with the aid of acid acceptors at a temperature between 0° and 160° C., especially between room temperature and the reflux temperature of the reaction mixture. Suitable acid acceptors include conventional bases, especially aliphatic amines, such as e.g. triethylamine or diisopropylamine, as well as alkali metal carbonates and their aqueous solutions.

The etherification can also be carried out in a two phase system using a catalyst and optionally in the presence of a solvent. Suitable bases include alkali metal hydroxides and alkali metal carbonates, either in solid form or in aqueous solution. Suitable solvents are the reactants themselves if they are liquids. Otherwise, there can be used substances which are immiscible with water and inert to the bases, such as for example aliphatic or aromatic hydrocarbons, such as for example hexane, benzene or toluene. Preferred catalysts are crown ethers, such as e.g. 1,4,7,10,13,16-hexaoxacyclooctadecane and quaternary ammonium salts, as described in Dehmlow and Dehmlow, Phase Transfer Catalysts, Weinheim 1980.

Generally the starting materials are used in stoichiometric amounts. An excess of one or the other can be used in some cases but without any particular advantage.

The reaction according to process variants (b) and (c) is generally carried out in the presence of a catalyst in a suitable solvent. The reaction temperature lies between 0° and 150° C., especially at the reflux temperature of the reaction mixture. Suitable solvents include for example dimethyl sulphoxide, halogenated hydrocarbons, such as for example methylene chloride and chloroform, aromatic hydrocarbons such as for example benzene, toluene, xylene, chlorobenzene and dichlorobenzene, as well as other solvents which are inert to the reactants, such as for example diethyl ether, tetrahydrofuran or dimethyl formamide.

Example of catalysts are acids, such as acetic acid or sulphuric acid, as well as acidic ion exchange resins.

The reaction according to process variant (d) is generally carried out with or without a suitable inert solvent. Suitable solvents include for example dimethyl sulphoxide, halogenated hydrocarbons, such as for example methylene chloride and chloroform, aromatic hydrocarbons such as for example benzene, toluene, xylene, chlorobenzene and dichlorobenzene, as well as other solvents which are inert to the reactants, such as for example diethyl ether, tetrahydrofuran or dimethyl formamide.

The reaction of compounds of formula IX and compounds of formula X according to process variant (e) is suitably carried out with the aid of acid acceptors at a temperature between 0° and 150° C., especially between room temperature and the reflux temperature of the reaction mixture. Suitable acid acceptors include conventional bases, especially aliphatic amines such as e.g. triethylamine or diisorpropylamine as well as alkali metal carbonates and their aqueous solutions.

The alkyation can also be carried out in a two phase system using a catalyst and optionally in the presence of a solvent. Suitable bases include alkali metal hydroxides and alkali metal carbonates, either in solid form or in aqueous solution. Suitable solvents are the reactants themselves if they are liquids. Otherwise, there can be used substances which are immiscible with water and inert to the bases, such as for example aliphatic or aromatic hydrocarbons, such as for example hexane, benzene or toluene. Suitable catalysts include crown ethers and quaternary ammonium salts.

Generally the starting materials are used in stoichiometric amounts. An excess of one or the other can be used in some cases but without any particular advantage.

The reaction according to process variant (f) is generally carried out in three stages without purification of the intermediates. Besides water there can be used as solvent any inert organic solvent. The reaction temperatures lie between $-20°$ and 100° C., especially between $-10°$ C. and room temperature.

The reaction according to process variants (g) and (h) is generally carried out at a temperature above 20° C., e.g. at 100° C. or at the reflux temperature of the reaction mixture. When one of the reactants is an anhydride, as with the compounds of formula XVI or XVII, the reaction is suitably carried out in the presence of an acid, such as acetic acid, for example in which acetic acid acts as solvent. It is however also possible for the reaction to take place in an inert solvent, such as e.g. dichloromethane or dimethyl sulphoxide, and to cyclise the intermediate addition product with an acid anhydride, such as for example acetic anhydride.

The reaction according to process variant (h) with compounds of formula XIX and XX is generally carried out in an inert solvent at a temperature between 20° C. and 150° C., especially at the boiling point of the solvent. Suitable solvents are for example aliphatic and aromatic, optionally chlorinated, hydrocarbons, such as petroleum ether, benzene, toluene, xylene, dichloromethane, chloroform, tetrachloromethane, 1,2-dichloroethane and chlorobenzene, as well as ethers, such as for example diethyl and di-n-butyl ether, methyl tert-butyl ether, tetrahydrofuran and dioxane, ketones, such as for example acetone, methyl ethyl ketone and methyl isopropyl ketone, as well as nitriles, such as acetonitrile and propionitrile, and sulphoxides, such as dimethyl sulphoxide or sulpholane.

The reaction according to process variant (i) is generally carried out in a solvent which is inert to the reactants, such as chloroform, ethers, such as dioxane or diethylene glycol dialkyl ethers, aliphatic hydrocarbons, such as cyclohexane or decane, optionally under the influence of a strong base, such as an alkali metal alcoholate or hydroxide, preferably in a 2 phase system in the presence of a phase transfer catalyst, such as those described in DEHMLOW AND DEHMLOW, Phase Transfer Catalysts, Weinheim 1980, at a temperature between room temperature and 200° C., especially at the boiling point of the solvent.

The compounds of the invention, prepared according to the above described processes, can be isolated in conventional manner, for example by distillation of solvent at normal or reduced pressure or by extraction.

An increased level of purity can be achieved as a rule by column chromatography as well as by fractional distillation.

The compounds of the invention are as a rule crystalline or viscous substances, which are to an extent highly soluble in halogenated hydrocarbons such as chloroform, sulphoxides, such as dimethyl sulphoxide, or esters, such as ethyl acetate.

The compounds of the invention can contain one or more asymmetric C atoms, The present invention includes the optically active forms and mixtures thereof. In the examples, unless otherwise stated, the racemate is obtained.

The starting materials of formula IV and XV can be obtained according to known processes. A possible synthesis route is shown in the following reaction scheme:

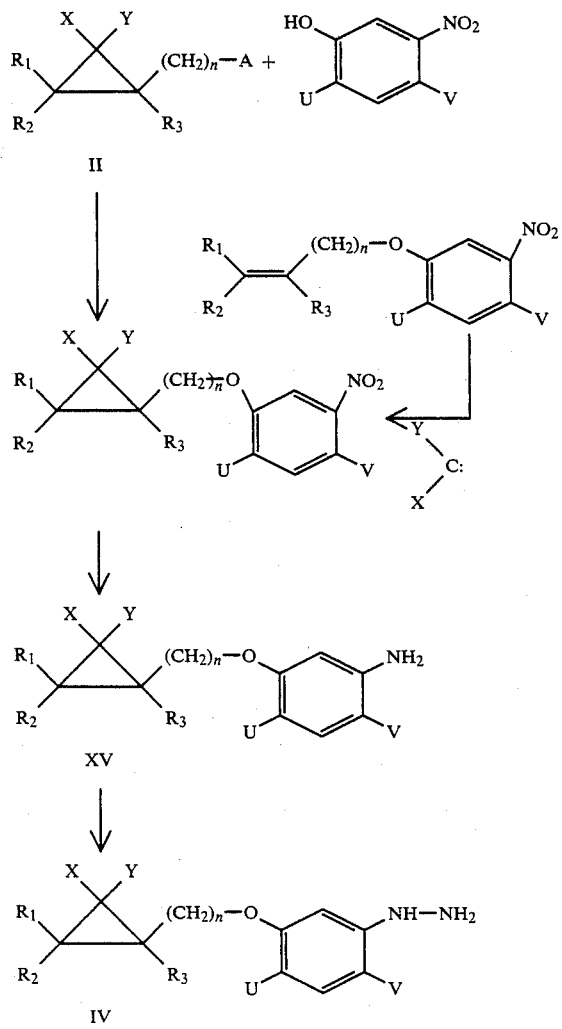

The preparation of the remaining starting materials is not described since they are known or can be obtained in an analogous manner to known processes.

The present compounds according to the invention have an excellent herbicidal activity against economically important mono- and dicotyledonous weeds. It is immaterial whether the compounds are sprayed before sowing, pre-emerence or post-emergence.

The compounds of the invention surprisingly possess outstanding compatibility with rice, wheat, soybeans, maize, cotton and barley.

The compounds of the invention can, for example, be used for combating weeds of the following plant species:

Dicotyledeonous weeds of the following families: Abutilon, Chrysanthemum, Brassica, Helianthus, Mentha, Sinapis, Lepidium, Galium, Stellaria, Anthemis, Chenopodium, Atriplex, Senecio, Portulaca, Ipomea, Matricaria, Galinsoga, Urtica, Amaranthus, Polygonum, Sesbania, Ambrosia, Sonchus, Solanum, Lamium, Veronica, Datura, Viola, Centaurea and Galeopsis;

Monocotyledenous weeds of the following species: Avena, Alopecurus, Echinochloa, Setaria, Panicum, Digitaria, Poa, Eleusine, Brachiaria, Lolium, Bromus, Cyperus, Agropyron, Sagittaria, Cynodon, Monochoria, Fimbristylis, Eleocharis, Ischaemum and Apera.

The use of the compounds of the invention is not limited to the weeds and crops mentioned above but can also be applied in a similar way to other plants.

The compounds are suitable also for use in higher amounts for total weed control, for example, in industrial and railway installations and in roads and open spaces. The compounds can also be used to combat weeds in permanent cultivations, such as for example forests, ornamental tree, fruit tree, vines, citrus, nut, banana, coffee, tea, rubber, oil-palm, cocoa, berry-fruit and hop-plantations.

The rates of use of the active material can very to a great degree. It depends essentially on the type of effect desired. In general, the quantities used lie between 0.01 and 5 kg of active material per hectare of land surface, preferably for example for combating weeds between 0.1 and 0.5 kg of active material per hectare.

When it is desired to broaden the spectrum of activity, other herbicides can also be added. Herbicidally active mixing partners suitable in this connection include for example, the active agents listed in Weed Abstracts, vol. 35, No. 3, 1986, under the heading "Lists of common names and abbreviations employed for currently used herbicides and plant growth regulators in Weed Abstracts".

The designated active materials or their mixtures are suitably used in the form of preparations such as powders, dusts, granules, solutions, emulsions or suspensions, with the addition of liquid and/or solid carriers and/or diluents agents and if desired, binding, wetting, emulsifying and/or dispersing adjuvants.

Suitable liquid carriers are, for example aliphatic and aromatic hydrocarbons, as well as cyclohexanone, isophorone, dimethyl sulphoxide, dimethylformamide and other mineral-oil fractions and plant oils.

Suitable solid carriers include mineral earths, e.g. bentonite, silica gel, talcum, kaolin, attapulgite, limestone, silicic acid and plant products, e.g. flours.

As surface-active agents there can be used for example calcium lignosulphonate, polyoxyethylenealkylphenyl ether, naphthalenesulphonic acids and their salts, phenolsulphonic acids and their salts, formaldehyde condensates, fatty alcohol sulphates, as well as substituted benzenesulphonic acids and their salts.

The percentage of the active ingredient(s) in the various preparations can vary within wide limits. For example, the compositions can contain about 10 to 90 percent by weight active ingredients, and about 90 to 10 percent by weight liquid or solid carriers, as well as, optionally up to 20 percent by weight of surfactant.

The agents can be applied in customary fashion, for example with water as the carrier in spray mixture volumes of approximately 100 to 1,000 l/ha. The agents can be applied using low-volume or ultra-low-volume techniques or in the form of so-called microgranules.

The preparation of these formulations can be carried out in known manner, for example by milling or mixing processes. Optionally, individual components can be mixed just before use for example by the so-called commonly used tank-mixing method.

Formulations can be prepared, for example, from the following ingredients.

(a1) Wettable powder
80% by weight, active material
10% by weight, kaolin
2% by weight, sodium N-methyl-N-oleyltaurine
8% by weight, calcium lignosulphonate (a2) Wettable powder
20% by weight, active material
35% by weight, bentonite
8% by weight, calcium lignosulphonate
2% by weight, sodium N-methyl-N-oleyltaurine
35% by weight, silicic acid (b) Paste
45% by weight, active material
5% by weight, sodium aluminium silicate
15% by weight, mixed polymerisation product from cetyl polyglycol ether with 8 moles of ethylene oxide
2% by weight, spindle oil
10% by weight, polyethylene glycol
23% by weight, water (c) Emulsifiable concentrate
20% by weight, active material
75% by weight, isophorone
2% by weight, calcium dodecylbenzenesulphonate
3% by weight, fatty alcohol polyglycol ether The following examples illustrate the preparation of compounds of the invention.

Preparation Example 1

N-[4-Chloro-5-(2,2-dichlorocyclopropylmethoxy)-2-fluorophenyl]-3,4,5,6-tetrahydrophthalimide (Compound No 1.1)

8.9 g (0.031 mol) 4-Chloro-2-fluoro-5-(2,2-dichlorocyclopropylmethoxy) aniline was dissolved in 12.5 ml acetic acid and 3.85 g 3,4,5,6-tetrahydrophthalic anhydride added. The mixture was heated under reflux for 3 hours, then poured into ice-water and extracted with ether. The ether phase was neutralised with aqueous sodium hydrogen carbonate, washed with saturated brine, dried over magnesium sulphate and the solvent removed. The residue was chromatographed on silica gel using a mixture of 9 parts hexane and 1 part ethyl acetate as eluent.

7.8 g (=75% of theory) of brownish crystals, m.p. 121°–122° C., were obtained.

The following compounds were prepared in an analogous manner:

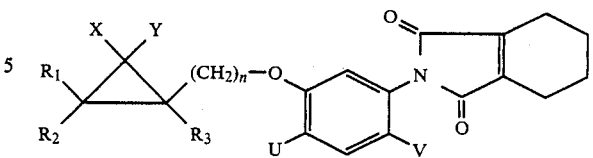

| Compound No. | $R_1$ | $R_2$ | $R_3$ | n | X | Y | U | V | Physical Constant |
|---|---|---|---|---|---|---|---|---|---|
| 1.2 | H | H | H | 1 | F | F | Cl | F | $n_D^{25} = 1.5375$ |
| 1.3 | H | H | H | 2 | F | F | Cl | F | $n_D^{24} = 1.5280$ |
| 1.4 | H | H | H | 2 | Cl | Cl | Cl | F | $n_D^{24} = 1.5555$ |

Preparation Example 2

2-[4-Chloro-5-(2,2-difluorocyclopropylmethoxy)-2-fluorophenyl]-4,5,6,7-tetrahydro-(2H)-1,2,3-triazolo[3,4-a]pyridin-8-ium-3-olate (Compound No 2.1)

4.6 g 4-Chloro-5-(2,2-difluorocyclopropylmethoxy)-2-fluoroaniline was suspended in a mixture of 9.7 ml concentrated sulphuric acid and 41.5 ml water and cooled to −10° C. A solution of 1.38 g sodium nitrite in 4.2 ml water was added dropwise at such a rate that the temperature of the reaction mixture did not rise above −5° C. After the addition it was stirred for a further hour at −5° C. and excess nitrous acid destroyed with urea until a test with iodine-starch paper was negative. The solution thus obtained was warmed to 0° C. and added dropwise to an ice-cold solution of 2.3 g pipecolic acid and 8.3 ml triethylamine in 27.7 ml water. After the addition it was stirred for a further hour at 0° C. and the reaction mixture extracted several times with methylene chloride. The organic phases were combined, dried over magnesium sulphate and the solvent evaporated. The residue was taken up in 40 ml ether and treated with 4.14 ml acetic anhydride and 2.07 ml pyridine. The mixture was stirred overnight at room temperature, then poured into ice-water and extracted with ethyl acetate. The organic phases were dried over magnesium sulphate and the solvent evaporated. The residue was chromatographed on silica gel using 95 parts ethyl acetate and 5 parts methanol as eluent.

0.9 g (=13.4% of theory) of crystals, m.p. 125°–127° C., were obtained.

Preparation Example 3

3-Chloro-2-]4-chloro-5-(2,2-difluorocyclopropylethoxy)-b 2-fluorophenyl]-4,5,6,7-tetrahydro-2H-indazole (Compound No 3.1)

5 g 4-Chloro-5-(2,2-difluorocyclopropylethoxy)-2-fluorophenylhydrazine was dissolved in 18 ml acetic acid, 2.85 ml ethyl cyclohexanone-2-carboxylate was added and the mixture heated under reflux for 8 hours. The mixture was then added to water and extracted with methylene chloride. The organic phases were neutralised with aqueous potassium hydrogen carbonate, washed with saturated brine and dried over magnesium sulphate. After evaporation of the solvent, there was obtained 8.4 g (=100% of theory) of crude product. This was treated with 3.6 ml phosphoryl chloride and the mixture heated under reflux. After 4 hours it was cooled, taken up in methylene chloride, washed with water and then saturated soda solution, dried over magnesium sulphate and the solvent evaporated. The residue was chromatographed on silica gel using a mixture of 95 parts dichloromethane and 5 parts methanol.

2.6 g (=35.6% of theory) of a brown oil, refractive index $n_D^{25}=1.5345$, was obtained.

The following compounds were prepared in an analogous manner:

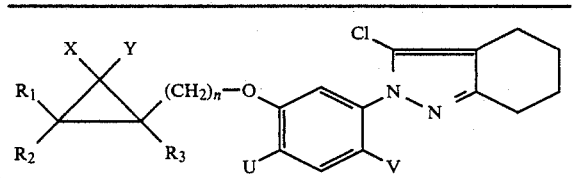

| Compound No. | $R_1$ | $R_2$ | $R_3$ | n | X | Y | U | V | Physical Constant |
|---|---|---|---|---|---|---|---|---|---|
| 3.2 | H | H | H | 1 | F | F | Cl | F | $n_D^{20} = 1.538$ |
| 3.3 | H | H | H | 1 | Cl | Cl | Cl | F | $n_D^{25} = 1.5713$ |
| 3.4 | H | H | H | 2 | Cl | Cl | Cl | F | $n_D^{25} = 1.5615$ |

Preparation Example 4

2-[4-Chloro-5-(2,2-difluorocyclopropylmethoxy)-2-fluorophenyl]-2,3,5,6,7,8-hexahydro-1,2,4-triazolo]4,3-a]pyridin-3-one (Compound No 4.1)

3 g 4-Chloro-5-(2,2-difluorocyclopropylmethoxy)-2-fluorophenylhydrazine was dissolved in 40 ml xylene and 2.4 g ethoxycarbonyl-2-piperiodone and 1 g phosphorus pentoxide was added. The mixture heated under reflux for 3 hours. It was then added to 100 ml water and the organic phase separated. The organic phase was neutralised with aqueous potassium hydrogen carbonate, dried over magnesium sulphate and the solvent removed. The residue was chromatographed on silica gel using ethyl acetate as eluent.

1.2 g (=23% of theory) of an oil, refractive index $n_D^{25}=1.5438$, was obtained.

The following compounds were prepared in an analogous manner:

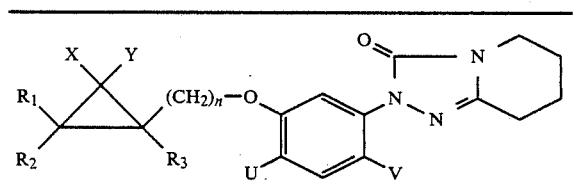

| Compound No. | $R_1$ | $R_2$ | $R_3$ | n | X | Y | U | V | Physical Constant |
|---|---|---|---|---|---|---|---|---|---|
| 4.2 | H | H | H | 1 | Cl | Cl | Cl | F | $n_D^{25} = 1.5655$ |
| 4.3 | H | H | H | 2 | Cl | Cl | Cl | F | $n_D^{25} = 1.5620$ |
| 4.4 | H | H | H | 2 | F | F | Cl | F | $n_D^{25} = 1.5332$ |

Preparation Example 5

2-[4-Chloro-5-(2,2-difluorocyclopropylmethoxy)-2-fluorophenyl]-3-thioxo-2,3,5,6,7,8-hexahydro-1H-imidazo[1,5-a]pyridin-1-one (Compound No 5.1)

2.9 g 4-Chloro-5-(2,2-difluorocyclopropylmethoxy)-2-fluorophenyl isothiocyanate was dissolved in 20 ml hexane and added dropwise to a solution of 1.5 ml ethyl piperidine-2-carboxylate in 10 ml hexane. The mixture heated under reflux for 2 hours. The solvent was removed and the residue was chromatographed on silica gel using a mixture of 3 parts hexane and 1 part ethyl acetate.

3.2 g (=82% of theory) of a viscous oil, refractive index $n_D^{40}=1.54$, was obtained.

Preparation Example 6

2-[4-Chloro-5-(2,2-difluorocyclopropylmethoxy)-2-fluorophenyl[-2,3,5,6,7,8-hexahydro-1H-imidazo[1,5-a]pyridine-1,3-dione (Compound No 6.1)

In an analogous manner to preparation Example 5, by reaction of 8.33 g 4-chloro-5-(2,2-difluorocyclopropylmethoxy)-2-fluorophenyl isocyanate and 4.69 ml ethyl piperidine-2-carboxylate in 100 ml hexane, there was obtained 7.7 g (=66% of theory) of a semicrystalline, whose nmr spectrum is as follows: d=1.1-2.4 ppm (m) 9H, d=2.7-3.15 ppm (m) 1H, d=3.85-4.4 ppm (m) 4H, d=6.87 (d 6 Hz) 1H, d=7.3 (d 9 Hz) 1H.

Preparation Example 7

3-[4-Chloro-5-(2,2-difluorocyclopropylmethoxy)-2-fluorophenyl]-5tert-butyl-1,3,4-oxadiazolin-2-(3H)-one (Compound No 7.1)

3 g 4-Chloro-5-(2,2-difluorocyclopropylmethoxy)-2-fluorophenylhydrazine hydrochloride was suspended in 18.5 ml toluene, treated with 3.6 ml triethylamine and the mixture stirred until the hydrochloride dissolved. Then, without cooling, 1.6 ml pivaloyl chloride was added slowly and the mixture stirred at room temperature for 2 hours. The reaction mixture was washed with water, saturated aqueous potassium bicarbonate and then again with water, dried over magnesium sulphate and the solvent removed. There remained, as a residue, 3.7 g of a red oil, that besides impurities, contained N'-[4-chloro-5-(2,2-difluorocyclopropylmethoxy)-2-fluorophenyl]pivaloylhydrazide. This crude product was dissolved in 22 ml of a 20% solution of phosgene in toluene, heated slowly to 100° C. and kept at this temperature for 3 hours. It was then cooled, treated with 20 ml methanol and concentrated. The residue was taken up in methylene chloride, washed twice with potassium bicarbonate and once with water, dried over magnesium sulphate and concentrated. To purify it, the crude product was chromatographed on silica gel using hexane/ethyl acetate=4:1 as eluent.

1.2 g (=24.5% of theory) of product, refractive index $n_D^{20}=1.5082$, was obtained.

Preparation Example 8

N-[4-Chloro-5-(2,2-difluorocyclopropoxy)-2-fluorophenyl]-3,4,5,6-tetrahydrophthalimide (Compound No 8.1)

1.2 g N-[4-Chloro-2-fluoro-5-vinyloxyphenyl)-3,4,5,6-tetrahydrophthalimide was dissolved in 5 ml diethylene glycol dimethyl ether, the mixture was heated to reflux and a solution of 2.8 g sodium chlorodifluoroacetate in 5 ml diethylene glycol dimethyl ether was added slowly. The mixture was heated under reflux for 5 hours, then separated from the sodium chloride, which formed, and the solvent removed. The residue was chromatographed on silica gel using a mixture of hexane/diethyl ether=1:1.

0.6 g (=43% of theory) of a crystalline substance, m.p. 105°-107° C., was obtained.

Preparation Example 9

1-[4-Chloro-5-(2,2-difluorocyclopropylmethoxy)-2-fluorophenyl]-4-difluoromethyl-3-methyl-1,2,4-triazolin-5-(4H)-one (Compound No 9.1)

8.2 g 4-Chloro-5-(2,2-difluorocyclopropylmethoxy)-2-fluorophenylhydrazine hydrochloride was dissolved in 163 ml water, treated first with 81 ml ethanol and then dropwise with a solution of 2.75 ml pyruvic acid in 81 ml water. The mixture was stirred for 1 hour and the precipitated product filtered and dried. There was obtained 7.9 g of the still slightly impure hydrazone that was used in this form.

The hydrazone was dissolved in 130 ml toluene, treated with 3.3 ml triethylamine and heated until the solution became clear. It was then cooled to ca. 35° C., 5.1 ml diphenyl phosphorazidate added dropwise and the mixture heated slowly to 75° C. It was maintained at this temperature until no more nitrogen evolved and then heated to reflux. After 12 hours it was cooled, washed three times with 10% soda solution, the aqueous phase washed twice with toluene and acidified. The product was extracted with toluene and the organic phase dried. After removal of the solvent, the product was chromatographed on silica gel using ethyl acetate as eluent. There was obtained 3.7 g (=35% of theory) of 1-[4-chloro-5-(2,2-difluorocyclopropylmethoxy)-2-fluorophenyl]-3-methyl-1,2,4-triazolin-5-(4H)-one The product, obtained from above, was dissolved in 300 ml cyclohexane, treated with 2.7 g potassium hydroxide and 2 g tetrabutylammonium bromide, the mixture heated to reflux and then chlorodifluoromethane passed in. After the reaction had finished (as shown by thin layer chromatography) the solution was decanted, washed twice with each of 1N hydrochloric acid and 10% aqueous soda, dried over magnesium sulphate and concentrated. The residue was chromatographed on silica gel with ethyl acetate and then once with methylene chloride.

80 mg (=2% of theory) of product, refractive index $n_D^{40} = 1.535$, was obtained.

Preparation of some starting materials

Preparation of 4-chloro-5-(2,2-difluorocyclopropylmethoxy)-2-fluoronitrobenzene 3.6 g 2-Chloro-4-fluoro-5-nitrophenol was dissolved in dimethylformamide and treated with potassium carbonate. The mixture was stirred at room temperature for one hour and then 3.3 g 2,2-difluorocyclopropylmethyl bromide added. It was the heated at 80° C. for 2 hours and added to water. The mixture was extracted with methylene chloride and the organic phase washed with saturated brine, dried over magnesium sulphate and concentrated. The residue was chromatographed on silica gel using a mixture of 3 parts hexane and 1 part ethyl acetate. There was obtained 5 g (=93% of theory) of yellow crystals whose nmr spectrum is as follows: $\delta = 1.1$–2.4 ppm (m) 3H, $\delta = 4.15$ ppm (d 7 Hz,tr 1.5 Hz) 2H, $\delta = 7.35$ ppm (d 10 Hz) 1H, $\delta = 7.5$ ppm (d 7 Hz) 1H.

The following compounds were prepared in an analogous manner:

| R₁ | R₂ | R₃ | X | Y | n | U | V |
|----|----|----|---|---|---|---|---|
| H | H | H | F | F | 2 | Cl | F |
| H | H | H | Cl | Cl | 1 | Cl | F |
| H | H | H | Cl | Cl | 2 | Cl | F |

Preparation of 4-chloro-2-fluoro-5-(2,2-difluorocyclopropylmethoxy)aniline 36.9 g 4-Chloro-2-fluoro-5-(2,2-difluorocyclopropylmethoxy)nitrobenzene in 600 ml ethanol was hydrogenated by the addition of 5 g of 10% palladium metal on activated charcoal at room temperature and normal pressure. After the uptake of hydrogen is complete the catalyst is filtered off, the solvent evaporated to give 29.3 g (=89% of theory) of an oil, whose nmr spectrum is as follows: $\delta = 1.1$–2.2 ppm (m) 3H, $\delta = 4.0$ ppm (d 10 Hz wide) 2H, $\delta = 5$ ppm (s wide) 2H, $\delta = 6.5$ ppm (d 7 Hz) 1H, $\delta = 7.0$ ppm (d 10 Hz) 1H.

The following compounds were prepared in an analogous manner:

| R₁ | R₂ | R₃ | X | Y | n | U | V |
|----|----|----|---|---|---|---|---|
| H | H | H | F | F | 2 | Cl | F |
| H | H | H | Cl | Cl | 1 | Cl | F |
| H | H | H | Cl | Cl | 2 | Cl | F |

Preparation of 4-chloro-2-fluoro-5-(2,2-difluorocyclopropylmethoxy)-phenylhydrazine 29.3 g 4-Chloro-2-fluoro-5-(2,2-difluorocyclopropylmethoxy)aniline was treated first with 45 ml half concentrated hydrochloric acid and then with 273 ml concentrated hydrochloric acid. It was then cooled to −10° C. and treated dropwise with a solution of 8.3 g sodium nitrite in 17 ml water at a such rate that the temperature of the reaction mixture did not rise above −5° C. It was stirred for 3 hours at −5° C. and the at −15° C., a solution of tin (II) chloride dihydrate in 34 ml concentrated hydrochloric acid added dropwise at such a rate that the temperature of the reaction mixture did not exceed −10° C. It was warmed at room temperature overnight. For the work-up, it was cooled to 0° C. and slowly neutralised with with 430 ml 32% caustic soda solution. The precipitated tin hydroxide slurry was separated by filtration through Celite and the filter cake washed with ether and the aqueous mother liquor extracted with ether. The combined organic phases were dried over magnesium sulphate and the solvent removed.

26 g(=100% of theory) of an oil is obtained, whose nmr spectrum is as follows: $\delta = 1.1$–2.3 ppm (m) 3H, δ=4.0 ppm (d 8 Hz wide) 2H, δ=6.85 ppm (d 7 Hz) 1H, δ=7.0 ppm (d 10 Hz) 1H.

The following compounds were prepared in an analogous manner:

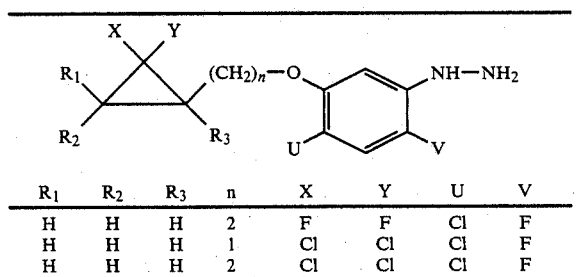

| $R_1$ | $R_2$ | $R_3$ | n | X | Y | U | V |
|---|---|---|---|---|---|---|---|
| H | H | H | 2 | F | F | Cl | F |
| H | H | H | 1 | Cl | Cl | Cl | F |
| H | H | H | 2 | Cl | Cl | Cl | F |

The following examples illustrate the activity of the compounds of the invention:

Use Example A

In the greenhouse, the compounds of the invention at a rate of 1 kg of active material per hectare, emulsified in 500 liters of water per hectare, were sprayed on the test plant species Matricaria and Viola in pre- and post-emergency treatments. 3 weeks after the treatment the results were appraised. All the compounds of the preparation Examples 1 to 9 caused destruction of the plants based on a scheme where 0=no activity and 4=destruction.

Use Example B

In the greenhouse, the listed plants were treated preemergently with the listed compounds at a rate of 0.1 kg of active material per hectare. For this purpose, the compounds were sprayed evenly over the plants as an emulsion in 500 liters of water per hectare. 3 weeks after the treatment, the compounds of the invention in comparison with known materials showed a high selectivity with excellent activity against the weeds.

| Compound | Br | So | Go | Gl | St | Ab | Ma | Vi | Av | Al | Ec | Se | Cy |
|---|---|---|---|---|---|---|---|---|---|---|---|---|---|
| No 4.1 | 4 | 4 | 0 | 0 | 4 | 4 | 4 | 4 | 4 | 4 | 4 | 4 | 4 |
| Comparison agents | | | | | | | | | | | | | |
| EP 61 741 | | | | | | | | | | | | | |
| No 1 | 2 | 3 | 1 | 1 | 3 | 3 | 4 | 4 | 2 | 2 | 2 | 4 | 1 |
| EP 105 721 | | | | | | | | | | | | | |
| No 1 | 3 | 4 | 2 | 1 | 3 | 4 | 4 | 4 | 2 | 3 | 4 | 4 | 0 |
| Oxadiazon | 0 | 3 | 0 | 0 | 2 | 3 | 2 | 4 | 0 | 2 | 1 | 3 | 0 |

Assessment scheme
0=no activity
1=slight damage
2=intermediate damage
3=heavy damage
4=total destruction Species
Br=Brassica sp.
So=Solanum sp.
Go=Gossypium hirsutum
Gl=Glycine max.
St=Stellaria media
Ab=Abutilon hybridum
Ma=Matricaria chamomilla
Vi=Viola tricolor
Av=Avena fatua
Al=Alopercurus myosuroides
Ec=Echinochloa crus-galli
Se=Setaria italica
Cy=Cyperus esculentus

Use Example C

In the greenhouse, the listed plants were treated postemergently with the listed compounds at a rate of 0.3 kg of active material per hectare. For this purpose, the compounds were sprayed evenly over the plants as an emulsion in 500 liters of water per hectare. 3 weeks after the treatment, the compounds of the invention in comparison with known materials showed a high selectivity with excellent activity against the weed.

| Compound | Br | So | Gl | He | St | Ab | Ma | Vi | Ch | Ip | Ze | Tr | Ho | Or | Sr | Se |
|---|---|---|---|---|---|---|---|---|---|---|---|---|---|---|---|---|
| No 1.1 | 4 | 4 | 0 | 4 | 4 | 4 | 4 | 4 | 4 | 4 | 0 | 0 | 0 | 0 | 0 | 3 |
| No 3.1 | 4 | 4 | 0 | 4 | 2 | 2 | 4 | 3 | 4 | 3 | 0 | 0 | 0 | 0 | 0 | 4 |
| No 3.2 | 4 | 4 | 0 | 3 | 4 | 3 | 4 | 4 | 4 | 4 | 0 | 0 | 0 | 0 | 0 | 4 |
| No 3.4 | 2 | 3 | 0 | 3 | 1 | 1 | 2 | 3 | 3 | 2 | 0 | 0 | 0 | 0 | 0 | 1 |
| No 4.3 | 3 | 4 | 0 | 3 | 3 | 4 | 4 | 3 | 4 | 4 | 0 | 0 | 0 | 0 | 0 | 3 |
| Comparison agent | | | | | | | | | | | | | | | | |
| Oxadiazon | 4 | 4 | 4 | 2 | 2 | 3 | 3 | 4 | 3 | 4 | 2 | 2 | 2 | 2 | 2 | 4 |

Assessment scheme
0=no activity
1=slight damage
2=intermediate damage
3=heavy damage
4=total destruction
Species
Br=Brassica sp.
So=Solanum sp.
Go=Gossypium hirsutum
Gl=Glycine max.
He=Helianthus annus
St=Stellaria media
Ab=Abutilon hybridum
Ma=Matricaria chamomilla
Vi=Viola tricolor
Ch=Chrusanthemum segetum
Ip=Ipomoea purpurea
Ze=Zea mays
Tr=Triticum aestivum
Ho=Hordeum vulgare
Or=Oryza sativa Sr=*Sorghum sativum*
Se=*Setaria italica*

Use Example D

In the greenhouse, the listed plants were treated postemergently with the listed compounds at a rate of 0.3 kg of active material per hectare. For this purpose, the compounds were sprayed evenly over the plants as an emulsion in 500 liters of water per hectare. 3 weeks after the treatment, the compounds of the invention showed good herbicidal properties.

| Compound | Ec | Ce | Cd | Fi |
|---|---|---|---|---|
| No 1.1 | 1 | 2 | 3 | 4 |
| No 1.2 | 4 | 2 | 4 | 4 |
| No 3.2 | 4 | 1 | 3 | 4 |
| No 4.3 | 3 | 1 | 3 | 4 |
| No 4.4 | 4 | 3 | 4 | 4 |
| No 5.1 | 1 | 1 | 3 | 3 |
| No 6.1 | 4 | 4 | 4 | 4 |

Assessment scheme
0=no activity
1=slight damage
2=intermediate damage
3=heavy damage
4=total destruction
Species
Ec=*Echinochloa crus-galli*
Cy=*Cyperus esculentus*
Cy=*Cyperus difformis*
Fi=*Fimbrystylis miliacea*

Use Example E

In the greenhouse, the compounds listed in the table were applied at rates also given in the table. For this purpose, the compounds were applied in containers with 1500 ml water (water application) The test plants were treated at the 2 to 5 leaf stage. Three weeks after the application, the damage to the plants was assessed.

As the table shows, the compounds of the invention are very active against important weeds of rice.

| Compound | Water application ppm | Ec | Ce | Cd | Fi | Sa | El |
|---|---|---|---|---|---|---|---|
| No 3.2 | 10 | 4 | 1 | 3 | 3 | — | — |
| No 4.3 | 10 | 4 | 1 | 4 | 4 | — | — |
| No 4.4 | 1 | 4 | 3 | 4 | 4 | — | — |
|  | 3 | 4 | 3 | 4 | 4 | — | — |
| No 5.1 | 1 | 4 | 2 | 2 | 2 | — | — |
|  | 3 | 4 | 4 | 3 | 4 | — | — |
| No 6.1 | 1 | 4 | 4 | 4 | 4 | — | — |
|  | 3 | 4 | 4 | 4 | 4 | — | — |
| No 7.1 | 3 | 4 | — | 4 | — | 3 | 4 |
| No 8.1 | 3 | 4 | — | 4 | — | 3 | 4 |
| No 9.1 | 3 | 4 | — | 4 | — | 3 | 4 |

Assessment scheme
0=no activity
1=slight damage
2=intermediate damage
3=heavy damage
4=total destruction
-=not tested
Species
Ec=*Echinochloa crus-galli*
Cy=*Cyperus esculentus*
Cy=*Cyperus difformis*
Fi=*Fimbrystylis miliacea*
Sa=*Sagittaria pusilla*
El=*Eleocharis acicularis*

We claim:

1. Halocyclopropyl compound of the formula I

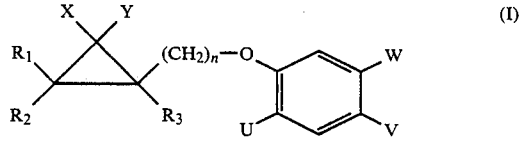

in which
$R_1$, $R_2$ and $R_3$, independently of each other, are hydrogen or $C_{1-4}$-alkyl,
X is hydrogen or halogen,
Y is halogen,
n is 0, 1, 2 or 3,
U and V are hydrogen or halogen, and
W is a heterocyclic group of formula

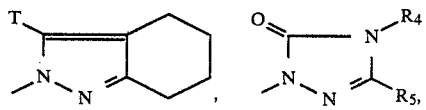

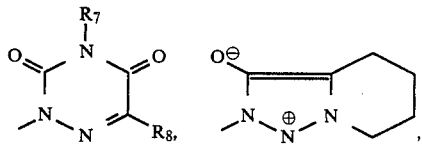

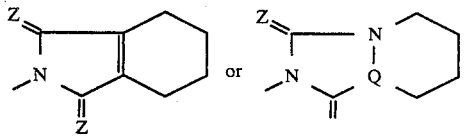

in which
T is halogen, $C_{1-4}$-alkyl, $C_{1-4}$-haloalkyl, CN or $OR_9$
Q is CH or N,
Z is O or S,
$R_4$, $R_5$, $R_7$ and $R_8$ are each a straight, branched or cyclic $C_{1-7}$-alkyl group optionally substituted by up to six halogen atoms, or
$R_4$ and $R_5$, can also together form a 4 to 7 membered ring that is saturated or unsaturated and can optionally be substituted by one to three methyl groups and one to six halogen atoms, and
$R_9$ is hydrogen, $C_{1-4}$-alkyl or $C_{1-4}$-haloalkyl.

2. A herbicidal composition characterised in that it comprises at least one compound according to claim 1 in admixture with an agriculturally acceptable diluent or carrier.

3. A method of combating weeds which comprises applying to the weed or its locus a herbicidally effective amount of a compound claimed in claim 1.

4. Halocyclopropyl compound according to claim 1 in which W is a heterocyclic group of formula

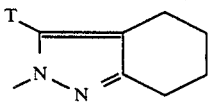

5. Halocyclopropyl compound according to claim 4 in which W is a heterocyclic group of formula

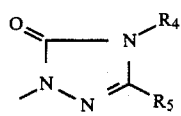

6. Halocyclopropyl compound according to claim 4 in which W is a heterocyclic group of formula

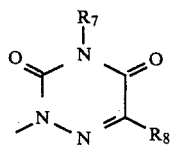

7. Halocyclopropyl compound according to claim 4 in which W is a heterocyclic group of formula

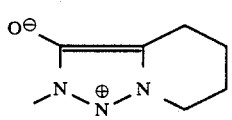

8. Halocyclopropyl compound according to claim 4 in which W is a heterocyclic group of formula

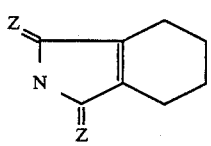

9. Halocyclopropyl compound according to claim 4 in which W is a heterocyclic group of formula

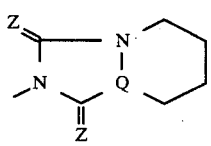

10. Halocyclopropyl compound according to claim 1 in which $R_1$, $R_2$ and $R_3$ are hydrogen, n is 1 or 2, X and Y are independently chlorine or fluorine, U is chlorine and V is fluorine.

11. Halocyclopropyl compound according to claim 10 in which (a) X and Y are chlorine and W is

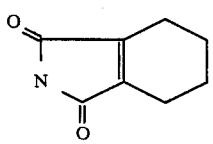

(b) X and Y are fluorine and W is

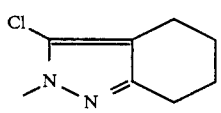

or (c) X and Y are chlorine and W is

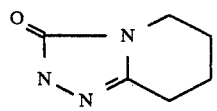

12. A herbicidal composition characterized in that it comprises at least one compound according to claim 11 in admixture with an agriculturally acceptable diluent or carrier.

13. A herbicidal composition characterized in that it comprises at least one compound according to claim 12 in admixture with an agriculturally acceptable diluent or carrier.

14. A method of combatting weeds which comprises applying to the weed or its locus a herbicidally effective amount of a compound claimed in claim 11.

15. A method of combatting weeds which comprises applying to the weed or its locus a herbicidally effective amount of a compound claimed in claim 12.

16. A method of combatting weeds according to claim 3 in which W is

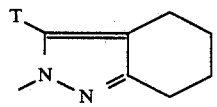

17. A method of combatting weeds according to claim 3 in which W is a heterocyclic group of formula

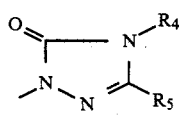

18. A method of combatting weeds according to claim 3 in which W is a heterocyclic group of formula

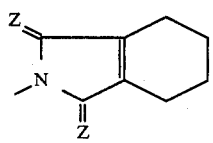

19. A method of combatting weeds according to claim 3 in which W is a heterocyclic group of formula

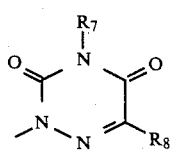

20. A method of combatting weeds according to claim 3 in which W is a heterocyclic group of formula

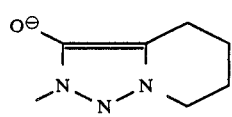
or
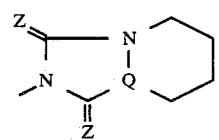
* * * * *